United States Patent [19]

Valleau et al.

[11] Patent Number: 5,028,100

[45] Date of Patent: Jul. 2, 1991

[54] METHODS FOR NONDESTRUCTIVE EDDY-CURRENT TESTING OF STRUCTURAL MEMBERS WITH AUTOMATIC CHARACTERIZATION OF FAULTS

[75] Inventors: A. Reed Valleau, Newton; Thomas A. O. Gross, Lincoln, both of Mass.

[73] Assignee: Trustees of the Thomas A. D. Gross 1988 Revocable Trust, Lincoln, Mass.

[21] Appl. No.: 366,607

[22] Filed: Jun. 15, 1989

[51] Int. Cl.$^5$ .................... G01N 27/72; G01R 33/12
[52] U.S. Cl. .................................. 324/232; 324/233; 324/238
[58] Field of Search ............... 324/226, 227, 232, 233, 324/237, 238, 240; 364/481, 506, 507, 550

[56] References Cited

U.S. PATENT DOCUMENTS 4,755,753  7/1988  Chern ................................. 324/237
4,763,274  8/1988  Junker et al. ...................... 324/238

OTHER PUBLICATIONS

Vernon, "Probe Properties Affecting the Eddy Current DNT of Graphite Epoxy", presented at Review of Progress in Quantitivate NDE at Williamsburg, Va. 7/1985.
Davis, "Multifrequency Eddy Current Inspection...", Materials Evaluation 1/1980, pp. 62-68.
Ouston, "Eddy Current Methods for Examination of Carbon Fibre Epoxy Resins", Materials Evaluation 11/1975, pp. 237-244.
Ouston "Carbon Fibre Reinforced Polymer and Nondestructive Testiny", British Journal of NDT 11/1973.
Vernon, "Eddy Current Nondestructive Inspection of Graphite Epoxy. . . " Report NSWCTR 87-148, 9/1987, pp. 1-55, A1-A2 & B1-B4.
McMaster et al., "Nondestructive Testing Handbook" 2nd ed. vol. 4, Electromagnetic Testing, 12/1986, pp. 48-51 & 634-636.
Vernon et al., "Eddy Current Inspection of Broken Fiber Flows. . . " presented at Univ. of California, San Diego, 7/1984.
Hagemaier, "Eddy Current Impedance Plane Analysis", Material Evaluation 2/1983, pp. 211-318.
Libby, "Broadband Electromagnetic Testing. . . ", Report BNWL953 of Contract AT(45-1)-1830 for the U.S. Atomic Energy Commission, 1/1969.
Libby, "Broadband Electromagnetic Testing. . . " Report HW59614 of Contract W-31-109-Eng52 for the U.S. Atomic Energy Commission, 1/1959.

Primary Examiner—Walter E. Snow
Attorney, Agent, or Firm—William D. Roberson

[57] ABSTRACT

Several phenomena which occur commonly in graphite composites, as well as other materials, and which affect the impedance of an eddy-current probe have been characterized on the complex impedance plane. An eddy-current method is disclosed by which a target material is stimulated at several frequencies, the impedance of the probe is measured and compared to the impedance of reference material, and the condition of the target material is determined. The method described is capable of finding the signatures of a number of conditions commonly found by eddy-currents, and can be programmed to find others, such as conductive and non-conductive plating thicknesses, and inclusions of material with relative ferrous materials. Because the method determines faults on the normalized impedance plane, it is capable of being used on other conductive materials in addition to graphite composites. A unique technique for accurately describing the size and shape of a fault with improved resolution using nondestructive eddy-current testing is also disclosed by which faults found by two anisotropic scans of the same material are mathematically combined.

13 Claims, 4 Drawing Sheets

METHODS FOR NONDESTRUCTIVE EDDY-CURRENT TESTING OF STRUCTURAL MEMBERS WITH AUTOMATIC CHARACTERIZATION OF FAULTS

The U.S. Government has a paid-up license in this invention and the right in limited circumstances to require the patent owner to license others on reasonable terms as provided for by the terms of:

Contract No. N60921-87-C-0112 awarded by the Whiteoak Laboratory of the Naval Surface Warfare Center.

BACKGROUND OF THE INVENTION

This invention relates to methods for the nondestructive eddy-current testing of formed articles such as structural members to determine the presence of hidden faults capable of causing the article to fail in conditions of intended use, and particularly to techniques for automatically locating and characterizing faults in a variety of physical members, including those composed of graphite-fiber composite materials.

While the invention is particularly useful for the nondestructive testing of graphite-fiber composite materials, the method offers advantages which can be used for a large variety of other materials.

Modern graphite fibers came about during a search for a filament to replace glass fibers as a stiffener in thermoset plastics. Glass fibers possess a number of important qualities including low density and great strength. One quality they lack, however, is stiffness. Graphite fibers have this and a number of other important qualities, but required that a practical method be found to produce them. In the early 1960s, experiments were carried out to thermally convert precursor materials into carbon fibers and fabrics. Within five years, carbon and graphite cloth were commercially available and were used extensively in phenolic composites for missile rocket motors. After five more years of development, commercial production of continuous fibers from rayon precursor yielded strong and uniform material. Today, rayon precursors have been almost entirely replaced by polyacrylonitrile (PAN) and pitch precursors.

Graphite fibers (in unidirectional arrays, woven cloths, and chopped fibers) are currently used with a variety of matrix materials. Epoxy (a thermoset plastic) is the most common matrix material, and graphite fibers are increasingly used with thermoplastics. In addition to epoxy and thermoplastics, carbon is sometimes used as the matrix material, yielding a material which can withstand temperatures in excess of 5000 degrees F.

Graphite composite materials offer superior strength and stiffness, dimensional stability, toughness, low weight, relatively low cost, and a variety of production methods. The outstanding design properties of graphite fibers in resin matrices are their high strength- and stiffness-to-weight ratios, and fatigue resistance. Graphite composites are, however, relatively brittle, have no yield behavior, and their resistance to impact is low. Graphite composite longitudinal strength ranges from 110,000 to over 450,000 psi. Longitudinal tensile modulus is in the range of 20–70 million psi. With proper selection and orientation of fibers, composites can be stronger and stiffer than equivalent thickness steel parts, and weigh 40 to 70% less.

Graphite composite materials today are widely used, with common applications including aircraft wings and wing structures for commercial and military aircraft, fuselage panels for military aircraft, cargo doors for space shuttles, light-weight components for racing bicycles, eye-glass frames, tennis racquets, skate-board decks, golf club shafts, skis, and structural components in high-performance racing sculls. Graphite in a carbon matrix is used for rocket nozzles and nose-cones, where performance is paramount and price is not an important consideration.

Dramatic increase in strength and stiffness is achieved by combining graphite-fiber reinforcements with tough matrix resins. Because these composites are frequently designed for structural optimization, their properties and performance can be critical, especially where failure can be life-threatening. Unlike the structure of most other materials, the built-up nature of laminates makes defects more likely to occur. Damage tends to be more upsetting to the balance of factors that affect material performance.

Techniques currently used most often to perform nondestructive testing on graphite composites include visual inspection, the tap test, radiography, and ultrasound. Visual inspection is limited to surface faults. Even impact damage is often sub-surface or visible only on the back side. The tap test provides a response which varies with material and structure, requires expertise, is highly subjective, and provides no quantitative information. Low energy radiography can pinpoint localized variations in fiber density in relatively thin components. Except in cases where longitudinal exposures are appropriate, the injection of radio-opaque material is required for the detection of delamination. In order to do this, the defect must already have been detected by other means and must be open to one surface.

Ultrasound testing is currently the most commonly used procedure for testing graphite composites nondestructively, and is used extensively by end users and manufacturers of graphite composite components alike. Ultrasonic nondestructive testing has the advantages that it is particularly well-suited to locating delaminations in graphite composites, that it can be relatively inexpensive to put in place, and that it is relatively easy to use and interpret. It does, however, have its limitations. First, while ultrasound responds to even the slightest material delaminations, it is insensitive to fiber breakage. Delaminations by themselves do not always indicate that a component is not serviceable. Secondly, it is messy. Immersion tanks or other couplants must be used, which means that either a component must be removed from service to be immersed in a tank, or that it be covered with a couplant before testing. In either case, the tested area will be in poor shape to receive a patch if a problem area is found after testing.

Since graphite fibers are relatively good electrical conductors, nondestructive eddy-current testing is another suitable technique for testing graphite composites. High-frequency magnetic fields cause eddy currents to flow in conductive material. In graphite composites, eddy currents flow in the graphite fibers, and are impeded only if fibers are broken. Eddy current nondestructive testing, therefore, responds to the feature which gives graphite composites its high tensile strength. Delaminations and simple matrix damage are less visible using eddy-current tests, but fiber damage is apparent with or without matrix damage.

Both eddy-current and ultrasonic techniques may be necessary for complete graphite-composite nondestructive testing, depending on the load-bearing requirements of the component. The load for components under tension is carried by fibers, and tensile strength is little affected by delaminations. Here, eddy-current testing would be an appropriate nondestructive testing tool. Loss of compressive strength in composites occurs when layers delaminate, a phenomenon to which ultrasound is particularly sensitive. For components which must survive both tension and compression, neither eddy-currents nor ultrasound alone provides an adequate indication of component serviceability, while a combination of the two techniques does.

BRIEF SUMMARY OF THE INVENTION

This invention provides a nondestructive eddy-current testing technique which can be successfully employed not only to locate but also to characterize faults in a variety of materials including graphite composites. It is useful with composites which vary substantially in composition, material conductivity, and thickness. The invention provides a method which can be carried out successfully by a technician with a minimum of training in eddy-current nondestructive testing, and with only general knowledge of the type of material being tested. The method herein described first detects and identifies certain phenomena common to the material to be tested. If an anomaly is detected, the nature of the fault is characterized. The method compares the material response to a standard, and, in the currently preferred embodiment, assumes that faults occur singly, and assumes unity relative permeability. In this method the member to be tested is subjected to eddy current excitation at a plurality of frequencies and the reactive effects are automatically compared at each frequency with a standard to characterize the nature of any anomalies detected. The following sections describe the method in greater detail together with a currently preferred system by which it may be implemented.

DETAILED DESCRIPTION OF THE INVENTION

It is useful in demonstrating the principles of this invention to provide a general purpose eddy-current nondestructive testing development station as hereinafter described. This station may have more capability than is required for a cost-reduced instrument of single ultimate purpose utility, but it is particularly important for its ability to demonstrate many features of this invention which are significant in the nondestructive eddy-current testing of graphite composites.

Figure 1:
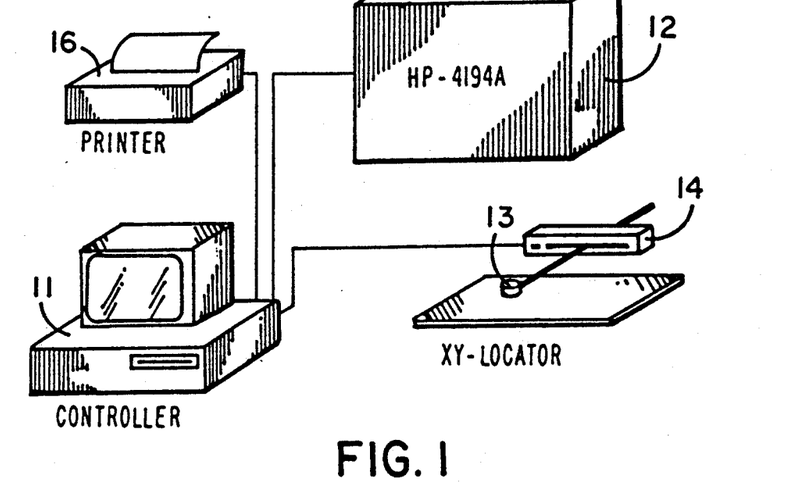
FIG. 1 is a block diagram illustrating a preferred system of functional elements useful in carrying out the invention.

FIG. 1 depicts a currently preferred development station comprising the following hardware: a controller with multicolor CRT display 11; a programmable complex impedance analyzer 12; a high frequency probe 13, preferably with flux directors; a position monitoring device 14 shown in contact with a sample panel to report or map the XY position of the probe on the panel 15; and a printer 16 for providing a readout in hard copy form from the controller 11.

The controller 11 shown is an IBM PS-2 Model 50 computer with VGA graphics capability and MS-DOS operating system. The computer is also be equipped with a math coprocessor to ease the computational bottleneck, and an IEEE-488 communications card to allow for efficient communications with the complex impedance analyzer 12. VGA graphics capability provides medium-high resolution (640×480) multicolor graphics. This computer has the advantage that it is small yet powerful, and is well supported by third-party hardware and software vendors. The software preferred as a best mode currently contemplated for the practice of this invention was written in C for ease of development and portability, and is listed in the appendix appended to this disclosure.

A Hewlett-Packard HP-4194A complex impedance analyzer 12 is used to perform the task of measuring probe impedance. This unit performs multifrequency impedance scans quickly and efficiently. It can operate from 10 Hz to 100 MHz, and may be controlled identically from its front panel or from a remote computer. The accuracy of the device is programmable, permitting the operator to choose from three levels of integration time, and eight levels of samples to be averaged to return a value. Finally, this analyzer has built-in compensation routines, enabling the unit to 'learn' the characteristics of the connecting cable and fixture. This makes precise impedance measurements possible, even at a considerable distance from the unit itself. As mentioned earlier, the 4194A impedance analyzer 12 and the IBM Model 50 computer 11 communicate over a parallel IEEE-488 bus, permitting rapid data transfer between the two devices.

The XY locator 14 could be one of several units currently available on the open market, for example a unit manufactured by SIGMA, because it is easy to attach to the target panel and is easy to operate. This unit measures distances optically, and does not require a microphone set-up such as is necessary for sonic units. XY accuracy is 0.01 inch, and is highly repeatable.

Initial experiments have shown that eddy-current nondestructive testing of graphite composites is indeed practical, but that there are several problems unique to the material. The most significant problem is the high resistivity of graphite composites, requiring test frequencies to be significantly higher for graphite composites than for metals. For example, the resistivity of pure aluminum is 2.62 micro-ohm cm, while typical graphite-epoxy composites have resistivities which range from 5,000-20,000 micro-ohm cm. Skin-depth frequencies for a 1-mm thick sample of aluminum is 6.6 kHz, while for a 1-mm sample of a graphite composite the range is from 12.6 to 50.6 MHz. Compared to eddy-current probes designed to be used with metals, those for graphite composites should be able to work at significantly higher frequencies. The size of the probes used for carbon-fiber-reinforced composites is the same as those used for aluminum panels when the two are scanned for similar faults. Eddy current is generally associated with the detection of small surface-breaking cracks in metals. The smaller the probe, the more sensitive the probe to small cracks. Also, the sensitivity is increased if the skin depth is less than the crack depth. If eddy-current nondestructive testing is used for the detection of a shallow back-surface-breaking fault in a panel of thickness T, the skin-depth of the frequency used for the inspection must be on the order of T for maximum sensitivity. In order to place this point at the point of maximum normalized resistance on the normalized complex impedance plane, probe pole separation and test frequency must be selected so that the ratio of the probe pole separation to material thickness (or probe pole separation to skin depth) is approximately 2.5:1.

To improve signal-to noise ratios, therefore, it is important to employ efficient probes which can be used at frequencies greater than 15MHz, and which direct as much flux as possible into the material being scanned. This is important not only for good signal-to-noise ratio, but also to illuminate material at depth with a significant amount of usable flux.

A probe core is desirable to shape and direct the magnetic flux from the probe 13, but material selection is also important because core materials should not have appreciable losses at the frequencies at which they are to be used. Because of the high frequencies necessary for eddy-current nondestructive testing of graphite composites, ferrites are the most practical core material available. Indeed, ferrites offer several advantages. They are inexpensive, readily available, and can be had in materials which have high permeability and low losses at high frequency. Ferrites can also be custom-molded to any shape desired. Nickel-zinc ferrites are particularly useful for carrying out this invention. Such material has a reasonably high initial permeability, low permeability change over a temperature range of 0 to 125 degrees C., low loss-factor, and is usable to 20MHz. Additionally, it is available in several useful shapes and sizes. Various sizes of these cores in both pot-core and toroidal shapes are readily available. The pot-cores may be obtained ungapped, and cut in half to make C-cores.

In addition to using ferrite cores to optimize probes for maximum flux penetration, flux directors may be incorporated. These flux directors are designed to eliminate as much flux as possible from completing magnetic paths outside the material to be scanned, while precluding the possibility of a shorted turn. Experiments on unshielded pot-core probes have shown that a significant amount of flux might not penetrate the target material. Flux directors in the form of silver shields can be used to minimize this problem. To determine the improvements afforded by these shields, the magnetic flux 12.7 mm (0.5 inches) in front of an unshielded pot core probe was measured. By adding flux directors, flux at that point increased by 40 percent.

To be of use in the field, cable assemblies should be at least 5 meters in length. Additionally, the resonant frequency of the probe assembly must be well above 50MHz so that resonant effects do not mask the impedance changes induced by faults when measured at 15MHz. The combination of these two requirements represents a formidable engineering challenge. The resonance frequency of an LC circuit is given by the formula:

$$F_{res} = \frac{1}{2 \times pi \times (LC)^{.5}} \quad \text{[Formula 1]}$$

where L and C are the circuit inductance and capacitance, respectively. The probes themselves are not a problem. It is possible to make very usable probes which generate a significant flux field with only 5 or 6 turns on a ferrite core. Even with shielding and internal capacitances, resonant frequencies can be well above 80 MHz. Problems occur when the cable assembly is attached to the probe. Any two-conductor cable connecting a probe to the impedance analyzer will have a measurable capacitance, and it is this capacitance which lowers the resonant frequency. To demonstrate the seriousness of this problem, consider a probe assembly with one meter of RG-174, a small-diameter flexible coaxial cable whose capacitance is specified to be 101 pf per meter. In order to keep the resonant frequency of the probe assembly above 50MHz, the inductance of the probe must be 100nH or less. A typical 1.1" pot core probe of nickel-zinc material develops this much inductance with approximately 0.5 turns of wire. A probe of this design does not produce nearly enough flux to be successfully employed for eddy-current nondestructive testing. In addition to that, a probe assembly 1-meter in length would not be very useful in the field.

The solution is to use three RG-174 coaxial cables instead of one, and a probe assembly which can be disconnected at the end of the cable harness. The compensation process involves the 4194A 'learning' the cable characteristics by measuring and recording impedances of (1) the probe assembly with the probe removed, (2) the probe assembly with a short circuit replacing the probe, and (3) the probe assembly with the probe replaced by a purely resistive load (50 ohms). Phase and amplitude errors introduced by the cable and fixture are then measured and stored, and are removed from subsequent measurements. Using this technique, only probe impedance characteristics are measured. Compensation must be performed each time the instrument is used to insure proper operation, but takes less than a minute to accomplish.

Preferred Method

There are several phenomena in graphite composites which can alter probe impedance but which may or may not affect material strength; these include areas of broken fibers, increasing or decreasing material thickness, lower and higher conductivity, and probe lift-off. The program software listed in the Appendix is capable of finding and characterizing faults and phenomena commonly found in graphite composites.

In the practice of this invention the preferred technique to separate fault-types compares the impedance of a probe on reference material to that on target material at three selected frequencies. These comparisons are performed on the normalized complex impedance plane. The conversion from the absolute R and X measurements of the probe on material ($R_{mat}$ and $X_{mat}$) to R and X in the normalized complex impedance plane ($R_{norm}$ and $X_{norm}$) requires knowledge of the unloaded or empty probe impedance ($R_{air}$ and $X_{air}$) and uses the formulas:

$$R_{norm} = (R_{mat} R_{air})/X_{air} \quad \text{[Formula 2]}$$

$$X_{norm} = X_{mat}/X_{air} \quad [\text{Formula 3}]$$

$R_{norm}$ and $X_{norm}$ for an unloaded probe is the point (0,1).

Figure 2:
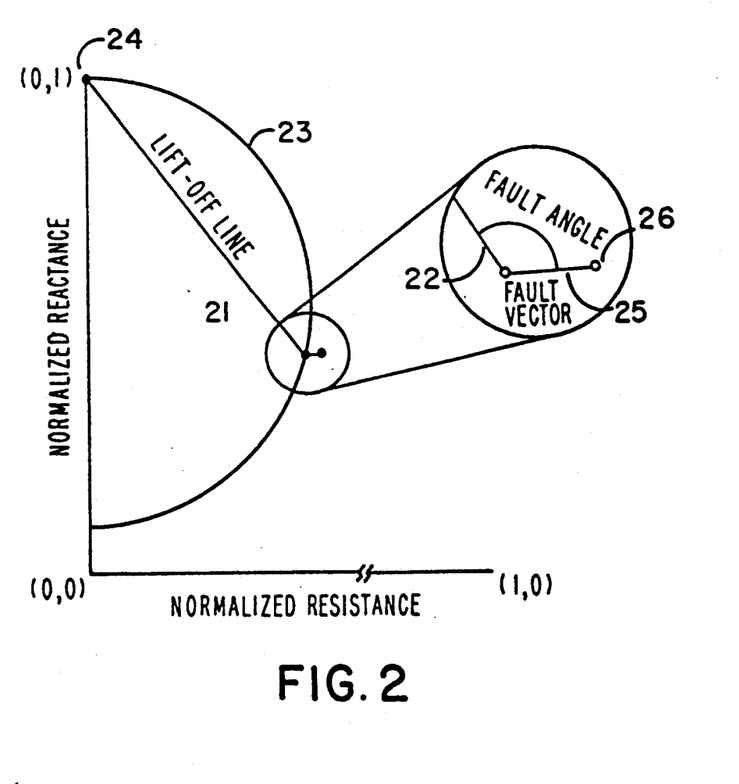
FIG. 2 is a typical normalized impedance plane diagram identifying certain principles of eddy-current testing of conductive materials.

FIG. 2 shows the normalized complex impedance plane diagram and the angles used in the fault-response analysis. Each entity is described as follows: A lift-off line 21 connects a point 22 on the normalized impedance plane curve 23 with the normalized reference point 24, and describes the locus of normalized probe impedance measurements as the probe is moved away from target material. The slope of the liftoff line 21 is a function of test frequency, probe size, material conductivity, and material thickness. In general, the better the probe-to-material coupling, the longer the liftoff line will be. Although such lines are actually slightly curved, a linear approximation is usually sufficiently accurate.

The impedance curve 23 is a locus of points which may be generated in several ways. A curve (or portion of a curve) will be generated if (1) the conductivity of the material under the probe changes, (2) the frequency applied to the probe is altered, or (3) the effective radius of the probe is changed.

Fault-response vectors such as the vector shown at 25 are directed line segments on the normalized impedance plane, with the head at the normalized fault-response point 26 and the tail at the normalized reference point 22. The fault-response vector magnitude is the length of the normalized line segment, and the fault-response angle is measured between the lift-off line 21 and the fault-response vector 25.

Figure 3:
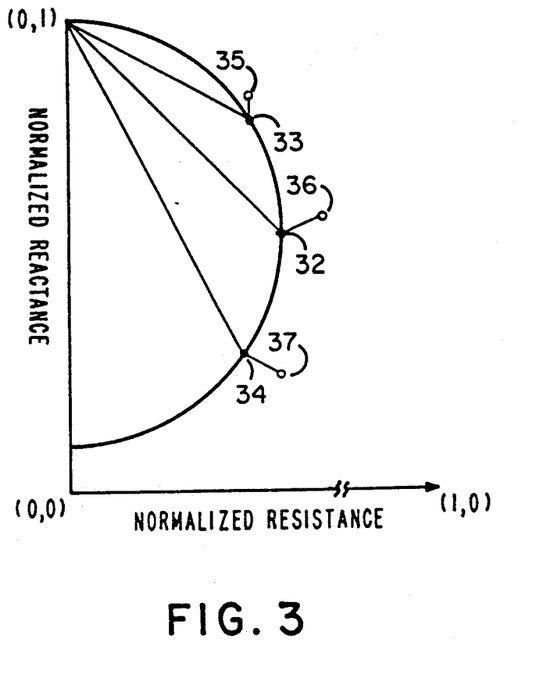
FIG. 3 is a normalized impedance plane diagram illustrating some characteristics of the use of multiple frequencies in the excitation of eddy currents in a member under test in accordance with this invention.

In the practice of this invention, probe impedances at three or more selected frequencies are particularly preferred to generate a unique and recognizable fault-response signature, as shown in FIG. 3. For optimum fault sensitivity, a middle frequency on the impedance curve 31 is chosen to correspond to the point 32 of maximum normalized resistance. The lower and upper frequencies, differing substantially from the middle frequency, are then calculated, preferably, to be approximately one-half and twice the middle frequency, respectively. These respective impedance points 33 and 34 tend to have a normalized resistance of approximately 90% of that of the middle frequency, and are spaced roughly the same distance above and below the normalized reactance of the middle frequency. This four-to-one range in frequencies is wide enough to generate unique fault-response signatures, and narrow enough that the impedance curve between the low and high frequencies can be approximated by a circular arc.

The operator must specify a reference before fault identification can be performed. The reference can be (1) a reference standard, (2) a point on the target material, (3) the arithmetic mean of all points collected (for C-scan only), or (4) a reference file which has been stored on disk. Once the reference has been established on the normalized impedance plane, data from the target material can be analyzed. If target material is different from the reference material, the probe impedances will be different as well. Probe impedances for the target material are normalized, and fault-response vectors generated. The pattern of fault-response vectors versus stimulation frequency is the fault-response signature, and fault-response signatures are used to determine the nature of the fault.

Fault-type analysis starts with a test for a change in material conductivity. As seen in FIG. 3, changes in conductivity move the fault points clockwise along the impedance curve 32 for increasing material conductivity, and counterclockwise for decreasing conductivity. If all fault-response angles are between 0 and 40 degrees or between 180 and 210 degrees, the software checks for lower and higher conductivity respectively. To perform this test the three reference points 33, 31, and 34 are considered to be points on a circle, and the center of this circle is calculated. All three reference points are equidistant from the calculated center, as would be any other points on the impedance curve 32 in the immediate vicinity. The distances between each fault-response point 35, 36, and 37 respectively, and the calculated center are determined. Fault points of material with lower or higher conductivity than the reference are the same distance to the center as the reference points to within a few percent. Additionally, the magnitude of the fault-response vector is proportional to the change in conductivity. In theory, the change in conductivity can be calculated from the fault-response vector magnitude, but for this project it was important only to be able to separate conductivity changes from actual material faults.

The other fault types are determined by using fault-response signatures alone, and are identified by the patterns given below:

| Probe Lift-off: | |
|---|---|
| Low-Freq. Fault-response Angle | < = 10 or > = 350 degrees |
| Mid-Freq. Fault-response Angle | < = 10 or > = 350 degrees |
| High-Freq. Fault-response Angle | < = 10 or > = 350 degrees |
| Increased Thickness | |
| Low-Freq. Fault-response Angle | > = 180 degrees |
| Mid-Freq. Fault-response Angle | > = Fault-response Angle 1 |
| High-Freq. Fault-response Angle | [immaterial] |
| Thinner Material or Embedded Fault: | |
| Low-Freq. Fault-response Angle | < = 140 degrees |
| Mid-Freq. Fault-response Angle | > = Fault-response Angle 1 |
| High-Freq. Fault-response Angle | [immaterial] |

If the anomaly meets none of these criteria, the fault type may not be known at the time. This can occur if, for example, an area of ferrous material is scanned. While the parameters listed above have been developed for graphite composites, they are general rules which can be used with other conductive materials, and which can be extended to include other phenomena not specifically listed here. The tests described below for Thick Material and Thinner Material or Embedded Fault assume that the target material is approximately one skin depth or less at low frequency. This assumption is almost always true for material with resistivity as high as graphite composites, and should be true in order to send useful eddy-currents to the back-side of the target material. The angles used to differentiate between increased Thickness and Thinner Material will be larger if the reference material is much thicker than a skin depth. Because the tests are performed by software, changes and improvements can be made and tested easily, and can be shared with users in the field by software upgrades.

To determine the fault-response signatures associated with each type of fault, faults may be synthesized and their magnitudes-vs.-frequency and angles-vs.-frequency graphed. For example, this process was performed using 5 thin graphite composite panels 305 mm by 305 mm (12 inches by 12 inches), each 2 mm (0.080 inches) thick. The probe had seven turns of #30 enameled wire on a shielded, C-core, nickel-zinc ferrite. The probe pole distance was 12.88 mm, and the probe assembly resonant frequency was 95.5 MHz. Frequencies were chosen using the criteria outlined above. Each graph derived shows the change in fault-response angle and magnitude as the frequency is swept from low to high. The low and high frequencies are one-half and twice, respectively, of the frequency corresponding to maximum normalized resistance on the reference material.

Figure 4:
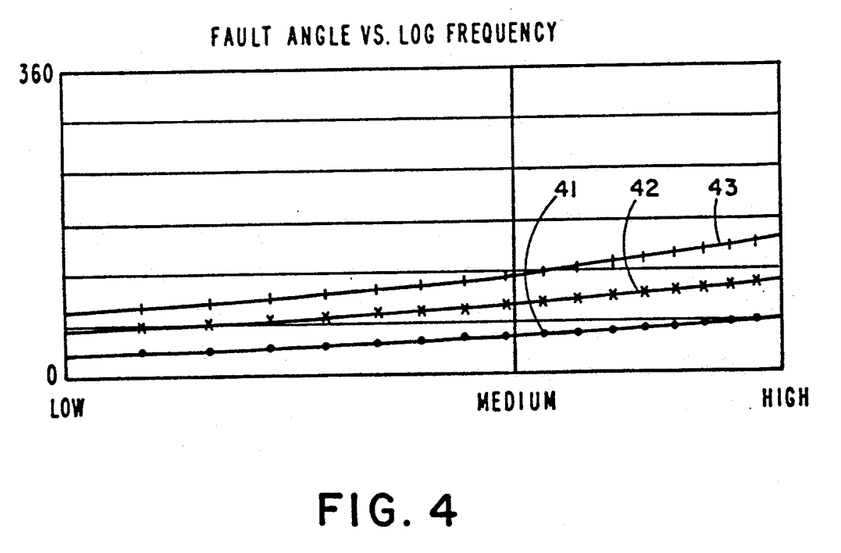
FIGS. 4 through 8 are graphical representations of fault-response signatures obtained in the practice of this invention, wherein FIG. 4 characterizes an embedded fault at three depths, FIG. 5 characterizes a material thinner than a reference standard, FIG. 6 characterizes a material thicker than a reference standard, FIG. 7 characterizes a material of higher conductivity with reference to the standard, and FIG. 8 characterizes a material of higher conductivity with reference to the standard.
Figure 5:
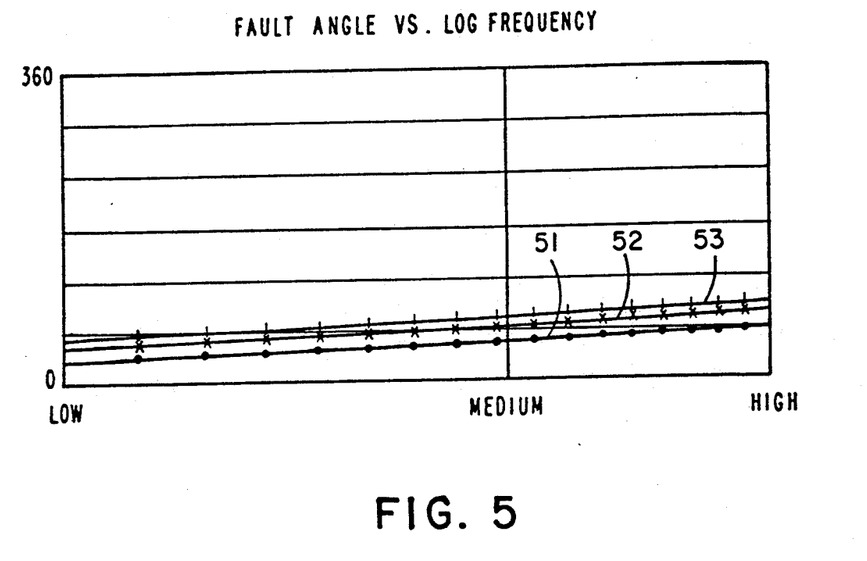

FIG. 4 shows Embedded Fault Signatures plotted as curves 41, 42, and 43 in terms of fault-response vector angles typical of an embedded fault at three depths. This fault type can be synthesized by using five assembled layers of thin graphite composite as a reference, and sequentially replacing layers two, three, and four with a non-conducting sheet of comparable thickness. FIG. 5 shows Thin Fault Signatures for material thinner than the reference. To synthesize this type of fault five layers can be used as a reference material; the curves 51, 52, and 53 show the fault-response angles and magnitudes for four, three, and two layers respectively. For both embedded faults and thinner material, the fault-response angles monotonically increase with frequency, and their fault-response angles at any frequency are useful to determine the depth of the fault.

Figure 6:
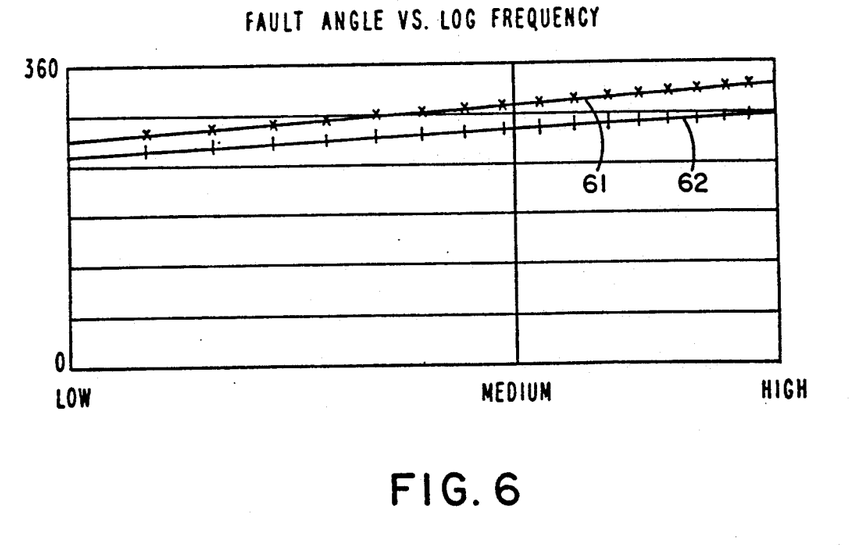
Figure 7:
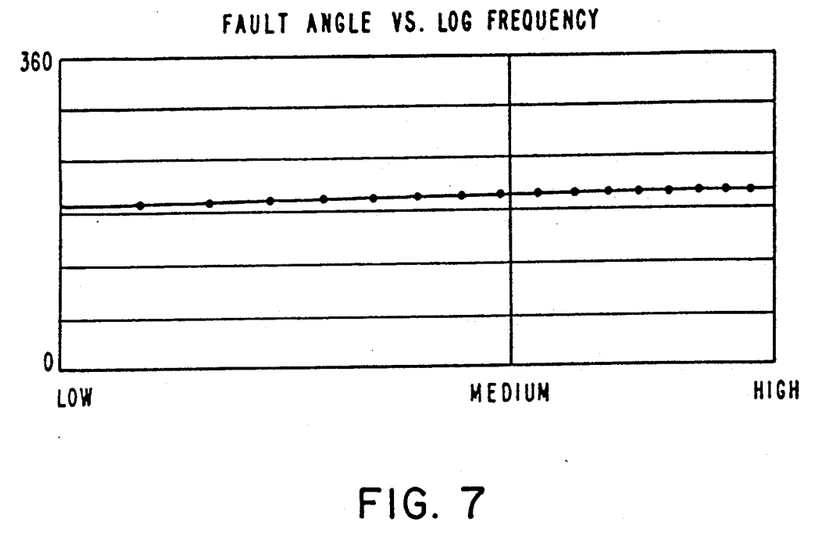
Figure 8:
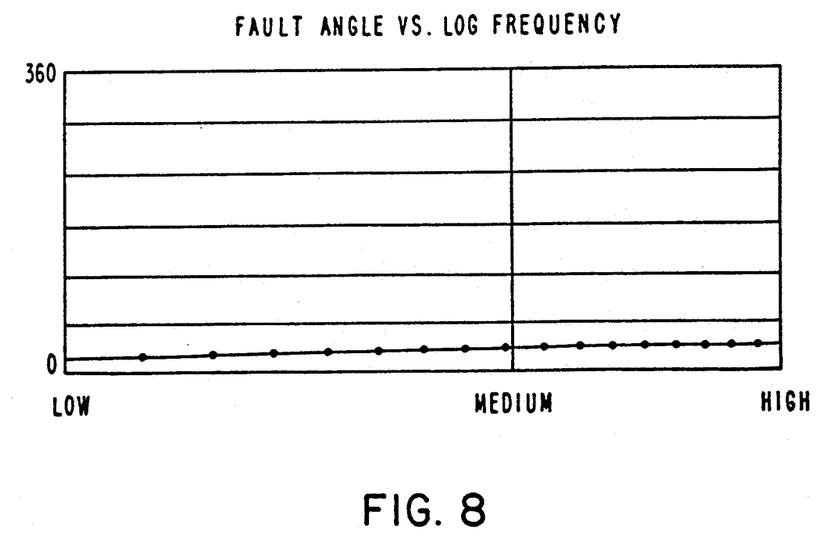

FIG. 6 shows Thick Fault Signatures for material thicker than the reference. To synthesize such a fault two layers can be used as a reference material; curves 61 and 62 show the fault-response angles for three and four layers respectively. FIG. 7 shows a High Conductivity Fault Signature of an area of higher conductivity and FIG. 8 a Low Conductivity Fault Signature of an area of lower conductivity in comparison to a reference standard.

It is in the recognition of these and other fault signatures indicating various patterns of anomaly with respect to a standard that the diagnosis of faults can be promptly made. When the software determines that the fault type is Thinner Material or Embedded Fault, a mathematical algorithm developed by Ms. Susan Vernon of NSWC is useful to determine the depth to the fault. The algorithm used to determine fault depth is described fully in a published document by her *Eddy Current Nondestructive Inspection of Graphite Epoxy Using Ferrite Cup Core Probes*, Report NSWC-TR-87-148, September 1987.

To establish a relationship between fault-response angle and fault depth, data was collected from faults in materials ranging widely in resistivity (including a titanium alloy, aluminum, and a carbon/carbon 3-d weave) for both flat-bottomed holes and saw cuts. This data was then graphed and subjected to a polynomial least squares fit, resulting in the following second-order polynomial:

*Fault-response Angle* $= A + B \times (ar)^{.5}/(skin\ depth)$
$\times (ar)/(skin\ depth) + C \times (ar)/(skin\ depth)^2$ [*Formula 4*]

where
Fault-response Angle is the Normalized Fault-response Vector Angle,
A, B, C were determined by Least Squares Fit to be $-24.73$, $113.21$, and $-17.49$ respectively
a is the depth from the material surface to the fault
r is the mean coil radius of the probe
skin depth is the standard skin depth of the target material at the frequency of interest. Skin depth, in mm, is given for non-magnetic materials by:
$50.29(rho/frequency)^{.5}$
rho is material resistivity in micro-ohm cm. For graphite composites, rho is a function of frequency.

Experience has shown that this relationship, although developed on materials of significantly lower material resistivity, can accurately determine the depth of embedded faults and thickness of material thinner than the reference material when the resistivity of the target material and probe radius are accurately known. Where these parameters are not accurately known, relative measures of fault depth and material thickness are achieved by using educated estimates.

There is a special advantage in using multiple frequencies to determine fault depth. At low frequencies, the fault-response angle decreases rapidly as the fault depth decreases, making it difficult accurately to measure fault depths for faults close to the surface. These faults can be better discerned by using higher frequencies which, however, can be inaccurate for measuring deeper faults. Application of the Vernon equation at multiple frequencies can improve the estimate of fault depths. In order to use the Vernon relationship accurately at multiple frequencies, material resistivity at all frequencies of interest must be known. Experiments on graphite epoxy composites show that material resistivity is a function of frequency. Experiments indicate that this relationship is essentially linear over the frequency range from 1 to 15 MHz, and that resistivity increases with frequency. Calculating material resistivity at any frequency within this range requires an accurate resistivity measurement at one frequency, and knowledge of the resistivity-vs.-frequency slope.

The results of the automatic detection and characterization of anomalies identified during a scan of a member under test may be visually displayed in different ways. For example, with a real-time eddy-current scope, which allows the operator to immediately see changes in normalized probe impedance at three frequencies when the probe is scanned over target material This mode allows an operator trained in eddy-current nondestructive testing to quickly scan a panel of questionable integrity and to determine whether further investigation is necessary. All of the hardware shown in FIG. 1 is used for real-time display, except for the XY spatial locator.

Another way to display the results visually is by the use of an eddy-current C-scan instrument, which requires data first to be collected from a panel, and which then processes the data to determine the location and nature of faults. Results are then displayed on the computer screen or sent to a printer. This mode simplifies interpretation of eddy-current results, determines the nature and extent of material faults, and enables the user to store data for reference at a later date.

Each data collection session, whether for real-time data display or for data collection for subsequent processing, begins with the selection of scan frequencies and collection of unloaded probe impedances at the selected frequencies. Frequency selection can be manual or automatic. Manual frequency selection requires the operator to select the high and low frequencies. The middle frequency is chosen as either the arithmetic or logarithmic mean of the low and high frequencies. The automatic mode is computer assisted, and helps the operator to choose optimum frequencies for the current probe and the material to be tested.

The software selects the optimum frequencies in the following manner. Scans are performed with the probe in air and on representative material from 0.2MHz. to 15MHz. The data is normalized and displayed. The frequency corresponding to the point with the greatest normalized resistance is selected as the middle frequency. The low and high frequencies are one-half and twice the middle frequency, respectively.

The software displays an impedance curve of the sample on the normalized impedance plane, highlighting the low, middle, and high frequencies chosen. The operator may modify the computer-selected frequencies before using them. Next, the software adds the synthesized impedance produced by calculating the circle defined by the three highlighted points. The first graphs can help the operator decide whether or not the current probe is an appropriate choice by the placement of the low and high impedance points. If the impedance curve, for example, does not extend past the point of highest resistance, a larger probe is called for. The second graph helps to decide if the low and high frequencies are correct by showing how closely the synthesized impedance curve matches the actual in the area of the frequencies to be used; a close match will improve the accuracy of the fault-type identification, while a poor match increases the chance of confusing embedded faults with conductivity noise.

A typical real-time display may have seven windows; one graphical and one text window for each of the three frequencies chosen by the operator, and one window to display commands and options. Each graphical window displays the reference point, lift-off line, synthesized impedance curve (generated by collecting reference data at frequencies slightly above and below the scanning frequencies), and the current fault-response vector. Each text window displays quantitative fault information, including fault-response magnitude, fault-response angle, and the ratio of distance from each fault point to the synthesized impedance curve center divided by the curve radius. The current normalized fault points are shown as the probe is moved over target material. At the same time, test frequencies, fault-response magnitudes and fault-response angles for each frequency are displayed in the fourth window. The software can optionally identify the type of fault being shown. Because the instrument is microprocessor-based, the window can be frozen or printed at any time. Moreover, because three user-selected frequencies are shown simultaneously, a knowledgeable user is presented with enough information to evaluate quickly the target material. Alarms can be set to indicate that one or more fault-response vectors have exceeded a predetermined magnitude. Several minutes of information can be recorded and played back at operator command, and data can be sent to a printer, either in real time or as recorded data is played back. The system can sample target material and display the results more than 15 times per second.

C-scan displays are generated in a two-step process. First, the raw data is collected and stored (in normalized form) on a disk or diskette. Once the data has been collected, a separate program may be used to process and display the data. To collect data, the operator is prompted to enter information about the probe, the target material, the size and resolution of the panel area to be scanned, and the name of the file to which the collected data will be written. After all parametric data has been entered, the operator begins the scanning processes. A display shows a representation of the panel to be scanned. As the operator moves the probe over the panel, probe impedance data is collected and stored to disk. Data stored to disk includes both probe impedance information for the frequencies chosen, and X and Y probe location data. The computer acknowledges that data has been collected from an area by changing the corresponding area displayed on the CRT from one color to another. The operator's responsibility, then, is simply to move the probe over the target material until the CRT indicates that the entire panel has been scanned. The software allows the operator periodically to save the data to disk to guard against power loss.

After all data has been collected and saved to disk, a second program is employed to interpret and display it. The result of this program is a C-scan of the target panel, showing areas of change in material thickness, change in material conductivity, and areas of suspected material fault. The faults within the panel are correctly identified, and fault depths are displayed in color, for example using Red (fault depth is calculated to be within the top one-third of the material thickness), Green (fault depth is calculated to be between one-third and two-thirds of the material thickness), and Blue (fault depth is calculated to be greater than two thirds of the material thickness). Within each color band, the intensity indicates the relative fault-response magnitude: greater magnitudes are shown as higher intensities. Data for an 80-sample by 80-sample scan is typically processed in under one minute.

It has been typical to perform eddy-current testing by scanning a member with a shielded pot-core probe. The fact that pot-core probes induce planar eddy-currents in all azimuthal directions is both an advantage and a disadvantage. It means that only one scan is necessary to find faults in any fabric layer, regardless of the orientation of the fibers. However, due to the nature of the pot-core eddy-current pattern, faults appear larger than they really are.

Another aspect of this invention concerns an approach to this problem by conducting similar scans with C-core probes to produce radially nonuniform eddy current excitations. Such a probe can be made from three nickel-zinc ferrite half-toroids, with an overall length of 9.5 mm, width of 10.0 mm, with pole separation of 7.5 mm. The resonant frequency of such a probe assembly is 85 MHz. Instead of the circular patterns of anomalies obtained from a pot core, the C-core anomalies detected appear elongated in the direction of the probe axis. This is due to the nature of the C-core eddy-current patterns. By scanning the same panel with the same C-core probe rotated 90 degrees from the initial scan, the circular faults are again elongated due to the nature of the C-core eddy-current patterns, but this time with a different angular orientation.

C-cores probes produce anisotropic flux patterns; they tend to be very sensitive to faults along their axes, while being blind to faults off axis. We theorized that the data from two orthogonal data sets could be mathematically compared to produce an image of improved resolution which more accurately depicts the sizes and shapes of embedded faults. Our observations have indicated that the two data sets agreed about the depth and magnitude of faults at points where faults did indeed exist, and disagreed elsewhere. Software written to combine two orthogonal data sets collected from C-cores, compare the results of the two scans on a point-by-point basis, and produce a CRT display which included only those points where fault depth and magnitude agreed to within ±10%. Combining two orthogonal C-core measurements in this manner results in a higher resolution and consequently more accurate fault image than can be obtained from a probe which produces an eddy current excitation pattern substantially uniform in azimuth.

We claim:

1. A nondestructive method for testing a physical member for the presence of unapparent anomalies, said member comprising a material which generates eddy currents in response to incident time-varying magnetic influences, which method comprises the step of:

subjecting each point to be tested on a surface of said member to periodically varying magnetic field at a plurality of frequencies;

sensing the responses to said field of the material of which said member is composed at each of said frequencies;

comparing the responses by said physical member at each of said points and at each of said frequencies to a reference to determine the existence of anomalies in such reactions;

determining the pattern of anomalies on a normalized impedance plane to develop a fault-response signature;

comparing said fault-response signature to a plurality of previously compiled fault-representative signatures each obtained on a normalized impedance plane at multiple frequencies and each representing a different type of fault to characterize the nature of any such fault; and identifying the location and type of such fault with respect to the surface of said physical member.

2. A nondestructive method for testing a physical member for the presence of unapparent anomalies, said member comprising a material which generates eddy currents in response to incident time-varying magnetic influences, which method comprises the steps of;

subjecting each point to be tested on a surface of said member to periodically varying magnetic field at at three selected frequencies differing substantially from each other and wherein the middle frequency is selected by normalized impedance plane analysis to correspond approximately to the maximum normalized resistance;

sensing the responses to said field of the material of which said member is composed at each of said frequencies;

comparing the respnoses by said physical member at each of said points and at each of said frequencies to a reference to determine the existence of anomalies in such reactions;

determining the pattern of anomalies on a normalized impedance plane to develop a fault-response signature;

comparing said fault-response signature to previously compiled fault-representative signatures obtained on a normalized impedance plane at multiple frequencies to characterize the nature of any such fault; and identifying the location of such fault with respect to the surface of said physical member.

3. The method of claim 2 wherein said middle frequency is approximately half that of another and twice that of the third.

4. A nondestructive method for testing a physical member for the presence of unapparent anomalies by generating eddy currents therein and detecting effects of such eddy currents, which method comprises the steps of:

compiling by normalized impedance plane analysis at a plurality of frequencies the signatures of a plurality of representative faults of recognizably different types which can occur in a representative physical member;

applying periodically varying magnetic fields at each point to be tested on a surface of a member to be tested, thereby to excite eddy currents therein;

varying the frequencies of such applied magnetic fields;

sensing the responses to such field by said member at each of said points and at a plurality of selected frequencies;

comparing the responses by the material of said physical member at each of said points and at each selected frequency of said field to each other and to a reference to determine the existence of anomalies in such reactions;

determining the pattern of anomalies on a normalized impedance plane to develop a fault-response signature;

comparing such fault-response signature to the aforesaid compiled signatures of representative faults to determine the type of fault represented by such fault-response signature; and identifying the locations and types of such faults on the surface of said physical member.

5. A nondestructive method for testing a physical member for the presence of unapparent anomalies by generating eddy currents therein and detecting effects of such eddy currents, which method comprises the steps of;

compiling by normalized impedance plane analysis at at least three selected frequencies differing substantially from each other the signatures of representative faults of recognizable types which can occur in a representative physical member and wherein the middle frequency is selected by normalized impedance plane analysis to correspond to the maximum normalized resistance;

applying periodically varying magnetic fields at each point to be tested on a surface of a member to be tested, thereby to excite eddy currents therein;

varying the frequencies of such applied magnetic fields;

sensing the responses to such field by said member at each of said points and at a plurality of selected frequencies;

comparing the responses by the material of said physical member at each of said points and at each selected frequency of said field to each other and to a reference to determine the existence of anomalies in such reactions;

determining the pattern of anomalies on a normalized impedance plane to develop a fault-response signature comparing such fault-responsive signature to the aforesaid compiled signatures of representative faults; and identifying the locations of such anomalies on the surface of said physical member.

6. The method of claim 5 wherein said middle frequency of approximately half that of another and twice that of the third.

7. A nondestructive method for testing a physical member for the presence of unapparent anomalies, said member comprising a material which generates eddy currents in response to incident time-varying magnetic influences, which method comprises the steps of:

subjecting each point to be tested on a surface of said member to a periodically varying, radially nonuniform magnetic field;

sensing the responses to said field of the material of which said member is composed;

rotating the direction of said magnetic field by a preselected angle at each of said points;

sensing the responses to said rotated field of the material of said member at each of said points;

comparing the responses by said physical member at each of said points at each selected angle of said field to each other and to a reference to determine the existence of anomalies in such reactions; and determining the locations of any such anomalies with respect to the surface of said physical member.

8. The method of claim 7 wherein the preselected angle through which said field is rotated is 90 degrees.

9. The method of claim 7 wherein said member is composed of a material having an inhomogeneous composition, the constituent component materials of such composition exhibiting differing responses to such time-varying magnetic influences, 10. The method of claim 7 wherein the periodically varying magnetic field is applied to said member at more than one selected frequency.

11. The method of claim 10 wherein the periodically varying magnetic field is applied to said member at three selected frequencies differing substantially from each other.

12. A nondestructive method for testing a physical member for the presence of unapparent anomalies by generating eddy currents therein and detecting the presence of such eddy currents, which method comprises the steps of: applying a periodically varying, radially nonuniform magnetic field at each point to be tested on a surface of said member;

varying the frequency of such applied magnetic field;

sensing the responses to such field by said member at each of said points;

rotating the direction of such magnetic field by a preselected angle of ninety degrees at each of said points;

sensing the responses to such rotated field by said member at each of said points;

comparing the responses by the material of said physical member at each of said points at each selected angle and frequency of said field to each other and to a reference to determine the existence of anomalies in such reactions;

determining the pattern of anomalies on a normalized impedance plane to develop a fault-response signature characterizing the nature of any such fault; and mapping the locations of any such anomalies with respect to the surface of said physical member.

13. The method of claim 12 further comprising the steps of:

synthesizing the signatures of representative faults of recognizable types which can occur in such a physical member; and comparing such fault-responsive signature to said synthesized signatures.

* * * * *